(12) United States Patent
Liao et al.

(10) Patent No.: US 9,521,985 B2
(45) Date of Patent: Dec. 20, 2016

(54) AUTOMATIC DETECTION OF CONTRAST INJECTION

(75) Inventors: Rui Liao, Princeton Junction, NJ (US); Yinxiao Liu, Iowa City, IA (US); Xudong Lv, Vancouver (CA)

(73) Assignee: Siemens Healthcare GmbH, Erlangen (DE)

( * ) Notice: Subject to any disclaimer, the term of this patent is extended or adjusted under 35 U.S.C. 154(b) by 1144 days.

(21) Appl. No.: 13/532,923

(22) Filed: Jun. 26, 2012

(65) Prior Publication Data

US 2013/0060132 A1 Mar. 7, 2013

Related U.S. Application Data

(60) Provisional application No. 61/513,097, filed on Jul. 29, 2011.

(51) Int. Cl.
*A61B 6/00* (2006.01)
*A61B 6/12* (2006.01)
*G06T 7/00* (2006.01)
*G06T 7/20* (2006.01)
*A61B 6/03* (2006.01)
*A61B 8/12* (2006.01)

(52) U.S. Cl.
CPC ............... *A61B 6/487* (2013.01); *A61B 6/12* (2013.01); *A61B 6/481* (2013.01); *G06T 7/0016* (2013.01); *G06T 7/20* (2013.01); *A61B 6/032* (2013.01); *A61B 6/469* (2013.01); *A61B 6/503* (2013.01); *A61B 6/5264* (2013.01); *A61B 8/12* (2013.01); *G06K 2209/057* (2013.01); *G06T 2207/10016* (2013.01); *G06T 2207/10121* (2013.01); *G06T 2207/30104* (2013.01)

(58) Field of Classification Search
CPC .......... A61B 6/032; A61B 6/12; A61B 6/469; A61B 6/481; A61B 6/487; A61B 6/503; A61B 6/5264; A61B 8/12; G06K 2209/057; G06T 2207/10016; G06T 2207/10121; G06T 2207/30104; G06T 7/0016; G06T 7/20
USPC ........................................ 382/132; 600/431
See application file for complete search history.

(56) References Cited

U.S. PATENT DOCUMENTS

| 8,655,041 B2 * | 2/2014 | John ...................... A61B 6/481 382/130 |
| 2001/0031919 A1 * | 10/2001 | Strommer ............ A61B 5/0066 600/424 |
| 2003/0123606 A1 * | 7/2003 | Mollus ................... A61B 6/466 378/42 |
| 2007/0189593 A1 * | 8/2007 | Yim ....................... A61B 6/481 382/128 |

(Continued)

*Primary Examiner* — Katherine Fernandez

(57) ABSTRACT

A method for automatically detecting the presence of a contrast agent in an x-ray image includes acquiring a preliminary x-ray image. A background image is estimated. The contrast agent is administered. A plurality of image frames is acquired. The background image is subtracted from each image frame. An image having a highest image intensity is selected. A predefined shape model is fitted to the selected image using a semi-global optimization strategy. The fitting of the shape model is used to fit the shape model to each of the subtracted images. A feature value is calculated for each image frame based on pixel intensities of each pixel fitted to the shape model for the corresponding subtracted image. An image frame of peak contrast is determined by selecting the image frame with the greatest feature value.

19 Claims, 19 Drawing Sheets

(56) References Cited

U.S. PATENT DOCUMENTS

2009/0088632 A1\* 4/2009 Khamene ................. A61B 5/06
600/424
2012/0128226 A1\* 5/2012 John ...................... A61B 6/481
382/132

\* cited by examiner (d)

AUTOMATIC DETECTION OF CONTRAST INJECTION

CROSS-REFERENCE TO RELATED APPLICATION

The present application is based on provisional application Ser. No. 61/513,097, filed Jul. 29, 2011, the entire contents of which are herein incorporated by reference.

TECHNICAL FIELD

The present disclosure relates to detection of contrast and, more specifically, to the automatic detection of contrast injection.

DISCUSSION OF THE RELATED ART

Aortic valve diseases include aortic stenosis in which the aortic valve fails to fully open and aortic insufficiency in which the aortic valve does not properly prevent the backflow of blood. It is estimated that aortic valve disease threatens the lives of 1.8% of the world's population. Aortic valve disease may be treated by replacing the aortic valve. Traditionally, aortic valve replacement is performed during open heart surgery.

New minimally invasive approaches to aortic valve replacement have been developed. Such approaches may be referred to as percutaneous aortic valve replacement (PAVR) and may include trans-catheter aortic valve implantation (TAVI). Examples of TAVI include trans-apical TAVI in which antegrade access is used where the catheter and the prosthesis are inserted via small incisions in the chest and the apex of the left ventricle, and trans-femoral TAVI in which the catheter is inserted retrogradely via the femoral artery and the aortic arch.

Both trans-apical TAVI and trans-femoral TAVI use X-ray angiographic and fluoroscopic imaging to guide the procedure. These images may be registered to a 3D model for greater structural detail in guidance. An exemplary approach for performing registration is described in U.S. patent application Ser. No. 13/211,716, filed Aug. 17, 2011, which is herein incorporated by reference in its entirety.

SUMMARY

A method for automatically detecting the presence of a contrast agent in an x-ray image includes acquiring a preliminary x-ray image of a region of interest of a subject prior to administration of the contrast agent. A background image is estimated based on the acquired preliminary x-ray image. The contrast agent is administered into the subject. A main set of x-ray images are acquired including a plurality of image frames. The estimated background image is subtracted from each image frame of the acquired main set of x-ray images to create a plurality of subtracted images corresponding to the plurality of image frames. A measure of image intensity is determined for each of the subtracted images. One or more of the subtracted images having highest image intensity is selected. A predefined shape model is fitted to the selected one or more subtracted images by first searching the entire subtracted image to identify a local area within which the predefined shape model is matched in translation using fixed scale translations, rotation, and scaling parameters and then fitting the predefined shape model within the identified local area. The fitting of the predefined shape model to the one or more subtracted images is used to fit the shape model to each of the plurality of subtracted images. A feature value is calculated for each image frame based on pixel intensities of each pixel fitted to the shape model for the corresponding subtracted image. An image frame of peak contrast is determined by selecting the image frame with the greatest feature value.

In fitting the predefined shape model to the selected one or more subtracted images, the shape model may be matched more coarsely in identifying the local area than in fitting the shape model within the identified local area.

The method may additionally include detecting a probe from within the preliminary x-ray image and generating a probe mask therefrom. In calculating the feature value for each image frame based on pixel intensities of each pixel fitted to the shape model for the corresponding subtracted image, pixels corresponding to the generated probe mask may be excluded.

The estimation of the background may be updated as the main set of x-ray images are acquired based on one or more most recent image frames that are classified as not including contrast.

The measure of image intensity for each subtracted image may include generating a non-linear histogram mapping of each subtracted image. Selecting one or more of the subtracted images having highest image intensity may include determining one or more highest histogram values.

The predefined shape model may be modified in accordance with an anatomical structure of the subject prior to fitting.

The predefined shape model may represent an aortic root.

The method may additionally include selecting a set of contrast frames from among the plurality of image frames that have a feature value that is sufficiently close to the frame of peak contrast. A set of non-contrast frames may be selected from among the plurality of image frames that have a feature value that is sufficiently far to the frame of peak contrast. A local classifier may be trained using the selected set of contrast frames as positive training data and using the selected set of non-contrast frames as negative training data. It may be determined whether each of the frames of the plurality of image frames that are neither sufficiently close to the frame of peak contrast nor sufficiently far to the frame of peak contrast are contrast frames or non-contrast frames using the trained local classifier.

A 3D image of the aortic root may be registered to the image frame that has been determined to be of peak contrast and the registered image may be displayed. The displayed registered image may be used as visual guidance in performing an interventional procedure.

A method for automatically detecting a contrast agent in an x-ray image includes acquiring a preliminary x-ray image of a region of interest of a subject known to exclude the contrast agent. A probe is detected from within the preliminary x-ray image and a probe mask is generated therefrom. A background image is estimated based on the acquired preliminary x-ray image. A first set of x-ray images including a plurality of age frames is acquired. The estimated background image is subtracted from each image frame of the acquired first set of x-ray images to create a plurality of subtracted images corresponding to the plurality of image frames. A measure of image intensity is determined for each of the subtracted images. One or more of the subtracted images having a highest image intensity is selected. Each of the selected images is compared with the estimated background image and determining that the first set of x-ray images does not include the contrast when each of the selected images are within a predetermined measure of similarity to the background image. When at least one of the selected images exceeds the predetermined measure of similarity to the background image, the following additional steps are performed: A predefined shape model is fitted to the selected one or more subtracted images, the fitting of the predefined shape model to the one or more subtracted images is used to fit the shape model to each of the plurality of subtracted images, a feature curve is calculated for set of x-ray images based on pixel intensities of each pixel fitted to the shape model for the corresponding subtracted image while excluding pixels corresponding to the generated probe mask, and frequency analysis is performed on the calculated feature curve to identify a case in which high contrast feature value is attributable to cardiac or respiratory motion. When it is identified that the first set of x-ray images does not have a high contrast feature value attributable to cardiac or respiratory motion, an image frame of peak contrast is determined by selecting the image frame with the greatest feature value.

In fitting the predefined shape model to the selected one or more subtracted images, the shape model may be matched more coarsely in identifying the local area than in fitting the shape model within the identified local area.

The method may additionally include detecting a probe from within the preliminary x-ray image and generating a probe mask therefrom. In calculating the feature value for each image frame based on pixel intensities of each pixel fitted to the shape model for the corresponding subtracted image, pixels corresponding to the generated probe mask may be excluded.

The estimation of the background may be updated as the main set of x-ray images are acquired based on one or more most recent image frames that are classified as not including contrast.

Determining the measure of image intensity for each subtracted image may include generating a non-linear histogram mapping of each subtracted image. Selecting one or more of the subtracted images having a highest image intensity may include determining one or more highest histogram values.

The predefined shape model may be modified in accordance with an anatomical structure of the subject prior to fitting. The predefined shape model may represent an aortic root.

The method may additionally include selecting a set of contrast frames from among the plurality of image frames that have a feature value that is sufficiently close to the frame of peak contrast. A set of non-contrast frames may be selected from among the plurality of image frames that have a feature value that is sufficiently far to the frame of peak contrast. A local classifier may be trained using the selected set of contrast frames as positive training data and using the selected set of non-contrast frames as negative training data. It may be determined whether each of the frames of the plurality of image frames that are neither sufficiently close to the frame of peak contrast nor sufficiently far to the frame of peak contrast are contrast frames or non-contrast frames using the trained local classifier.

A 3D image of the aortic root may be registered to the image frame determined to be of peak contrast and displaying the registered image. The displayed registered image may be used as visual guidance in performing an interventional procedure.

A computer system includes a processor and a non-transitory, tangible, program storage medium, readable by the computer system, embodying a program of instructions executable by the processor to perform method steps for registering a 2D fluoroscopic image of an aortic root to a 3D image of the aortic root. The method includes acquiring a 3D image of the aortic root of a subject. A preliminary x-ray image of the aortic root of the subject is acquired prior to administration of a contrast agent. A background image is estimated based on the acquired preliminary x-ray image. The contrast agent is administered into the subject. A main set of x-ray images including a plurality of image frames is acquired. The estimated background image is subtracted from each image frame of the acquired main set of x-ray images to create a plurality of subtracted images corresponding to the plurality of image frames. A measure of image intensity is determined for each of the subtracted images. One or more of the subtracted images having a highest image intensity is selected. A predefined shape model of an aortic root is fitted to the selected one or more subtracted images by first searching the entire subtracted image to identify a local area within which the predefined shape model is matched in translation using fixed scale translations, rotation, and scaling parameters and then fitting the predefined shape model within the identified local area. The fitting of the predefined shape model to the one or more subtracted images is used to fit the shape model to each of the plurality of subtracted images. A feature value for each image frame is calculated based on pixel intensities of each pixel fitted to the shape model for the corresponding subtracted image. An image frame of peak contrast is determined by selecting the image frame with the greatest feature value. The 3D image of the aortic root is registered to the image frame determined to be of peak contrast.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
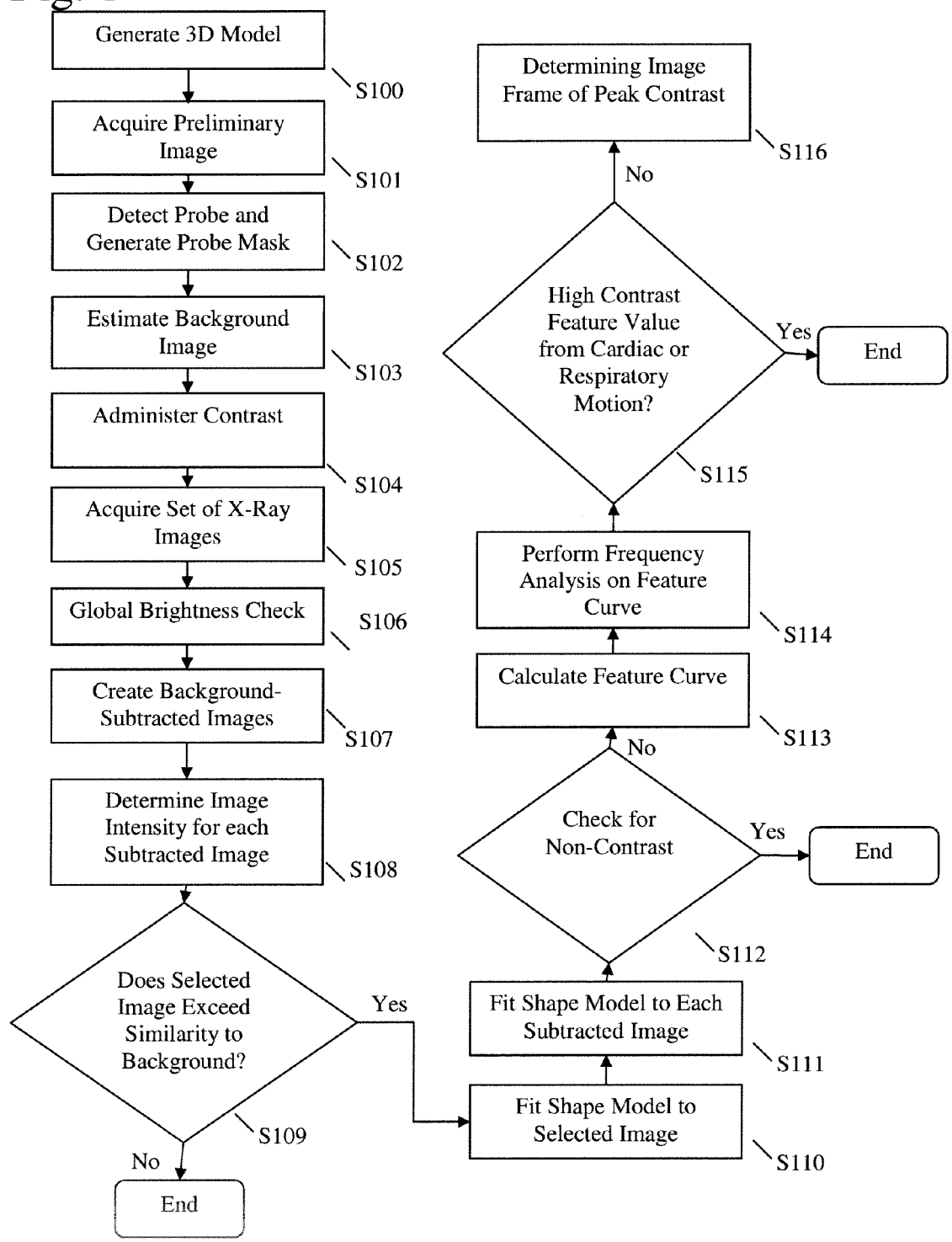
FIG. 1 is a flow chart illustrating a method for performing automatic contrast detection according to exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention relate to the use of three-dimensional (3D) models to support TAVI procedures in which a 3D aortic model is overlaid onto fluoroscopy to provide anatomical details and more automatic and accurate C-ARM angulation for optimal valve deployment. The 3D model may be produced, for example, using a computed tomography (CT) scanner, a magnetic resonance (MR) image scanner, or by other suitable modalities.

Accurate overlay of 3D models onto fluoroscopy may utilize 2D/3D registration between the 3D model and the fluoroscopy. This registration may be achieved by matching the 3D model to the fluoroscopic image frames with contrast injection showing the aortic root. Identification of the frames of the fluoroscopy showing contrast may be performed manually; however, exemplary embodiments of the present invention provide approaches for automatically identifying contrast-enhanced fluoroscopic image frames so that optimal frames may be selected for use in registering the fluoroscopic image data to the 3D aortic model or for other purposes such as, for example, for performing motion compensation in image sequences.

Exemplary embodiments of the present invention provide for the automatic detection of contrast injection into the aortic root on fluoroscopy and/or angiography. The proposed method may be used to automatically trigger 2D/3D registration, to detect anatomical landmarks during TAVI procedures, and/or to compensate for motions such as patient movement, aortic root movement due to insertion of devices, and position change of the heart during rapid pacing. However, the disclosure should not be seen as limited to automatic detection of contrast injection solely for the purposes of TAVI procedures, and indeed automatic detection of contrast injection may be used for other purposes as well without departing from the disclosure.

Automatic detection of contrast injection, according to exemplary embodiments of the present invention, may provide for a more seamless workflow for motion compensation during TAVI, and this may accordingly increase the efficiency and efficacy of these relatively complicated hybrid-OR applications that may involve a large number of staff, equipment and steps.

In addition to detecting whether there is contrast injection in a fluoroscopy or angiography sequence, exemplary embodiments of the present invention may automatically detect a range of frames, of a sequence of frames, where the aortic root and/or ascending aorta are filled with contrast agent. The detected range of frames may then be used for 2D/3D registration and/or subsequent motion compensation.

Exemplary embodiments of the present invention may utilize a likelihood ratio test-based method for contrast detection in which the contrast injection may be detected across a wide range of patient data with the same parameter setting. Exemplary embodiments of the present invention extend this approach to handle general and difficult cases, such as faint contrast and dark ultrasonic probe partially occluding the aortic root that can result in false negatives, as well as the image content variation due to respiration, heart beating and sudden global brightness change that often introduce false positives. In addition, a semi-global registration method may be implemented to align the aorta shape model, to increase the robustness of the detection algorithm in practical use with respect to the moderately different selection of the ROI around the aorta.

FIG. 1 is a flow chart illustrating a method for performing automatic contrast detection according to exemplary embodiments of the present invention. First, a 3D model of the aortic root may be generated (Step S100). Generation of the 3D model may be performed, for example, by acquiring a 3D medical image such as an MRI or a CT scan. Alternatively, generation of the 3D model may be obtained with the use of an X-ray imager placed on a C-arm that captures imagery of the aortic root from at least two different angles so that the X-ray images may be combined to form the 3D model. This step may be performed where automatic detection of contrast is used for the purpose of 2D/3D registration, however, where automatic detection of contrast is for another purpose, the step of generating the 3D model may be omitted.

One or more preliminary X-ray image frames may be acquired (Step S101). The preliminary X-ray image frames may be acquired, for example, using a fluoroscope by capturing a limited number of frames. Acquisition of the preliminary X-ray image frame(s) may be performed prior to the administration of the radiocontrast agent so that image frame(s) that are known to exclude the contrast may be obtained.

Figure 5A:
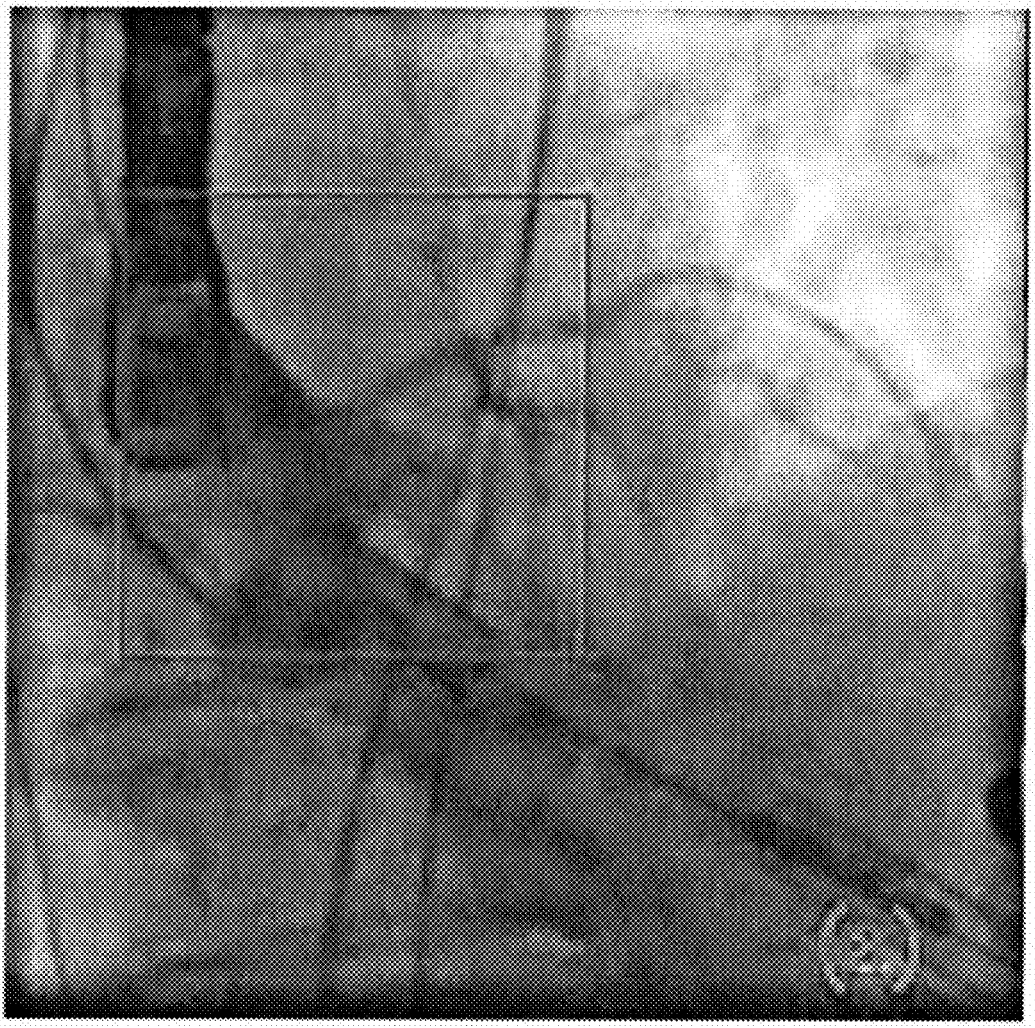
FIGS. 5(a)-(e) illustrate ultrasound probe detection in accordance with exemplary embodiments of the present invention.
Figure 5B:
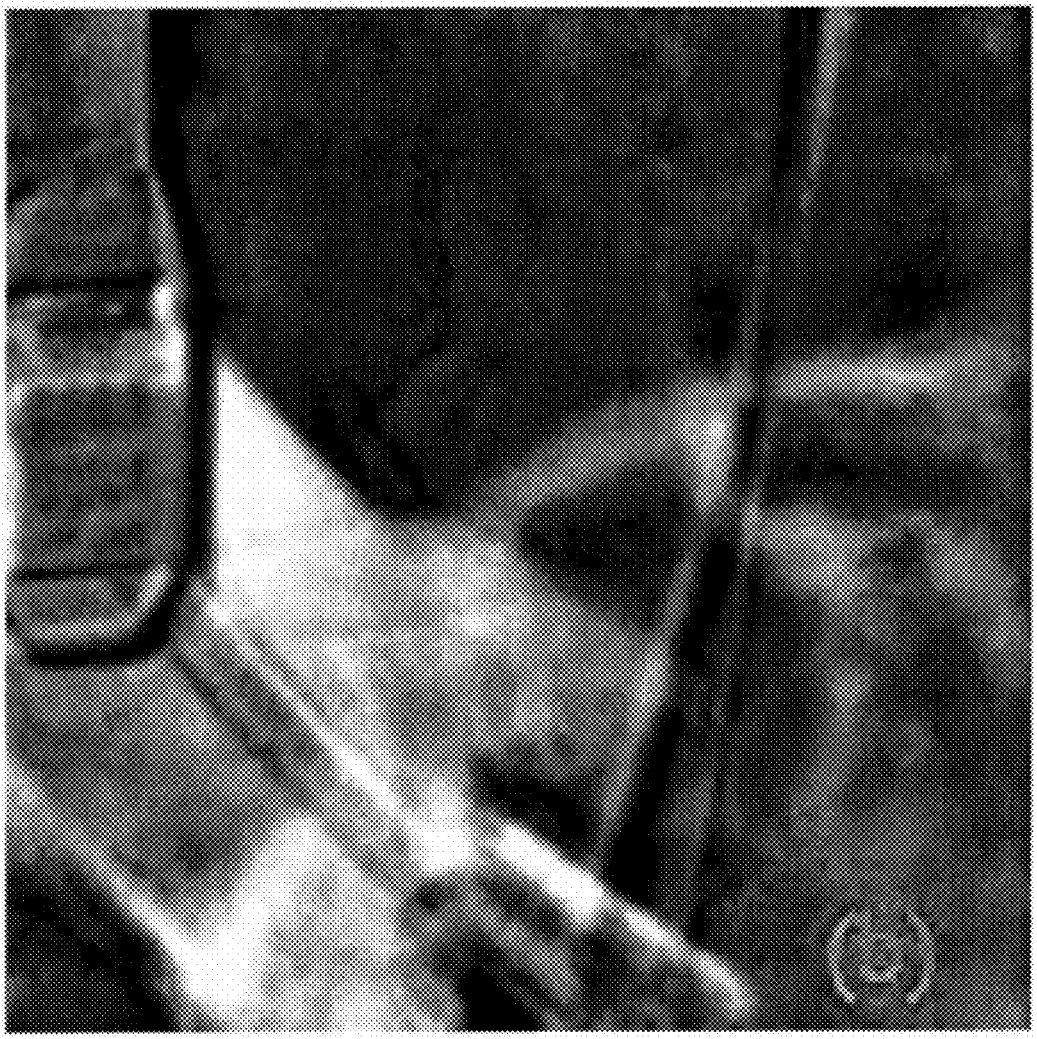
Figure 5C:
Figure 5D:
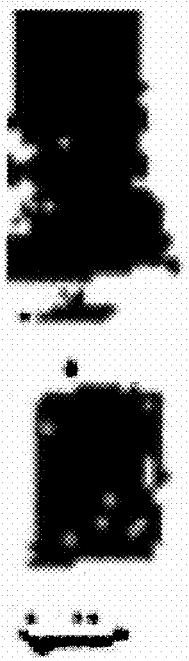

During the surgery, a trans-esophagus ultrasound probe (TEE) may be inserted into the patient body through the esophagus. Depending on the C-Arm angulations, the probe in the X-ray image may partially occlude the aortic root, for example, as shown in FIG. 5(a) which is an illustration of an ultrasound probe detection from an original x-ray image slice with contrast. The rectangle signifies the ROI shown in FIGS. 5(b)-(d) where FIG. 5(b) illustrates a mean contrast group image. FIG. 5(c) illustrates exemplary registration results of SM, and FIG. 5(d) illustrates the detected ultrasound probe mask.

The TEE probe may therefore introduce false negatives for some sequences if the peak value is close to the threshold of contrast detection. Accordingly, exemplary embodiments of the present invention may detect the TEE probe from the acquired preliminary X-ray image and generate a probe mask (Step S102) which may latter be used to exclude the TEE probe from the calculation of the contrast feature value.

Figure 5E:
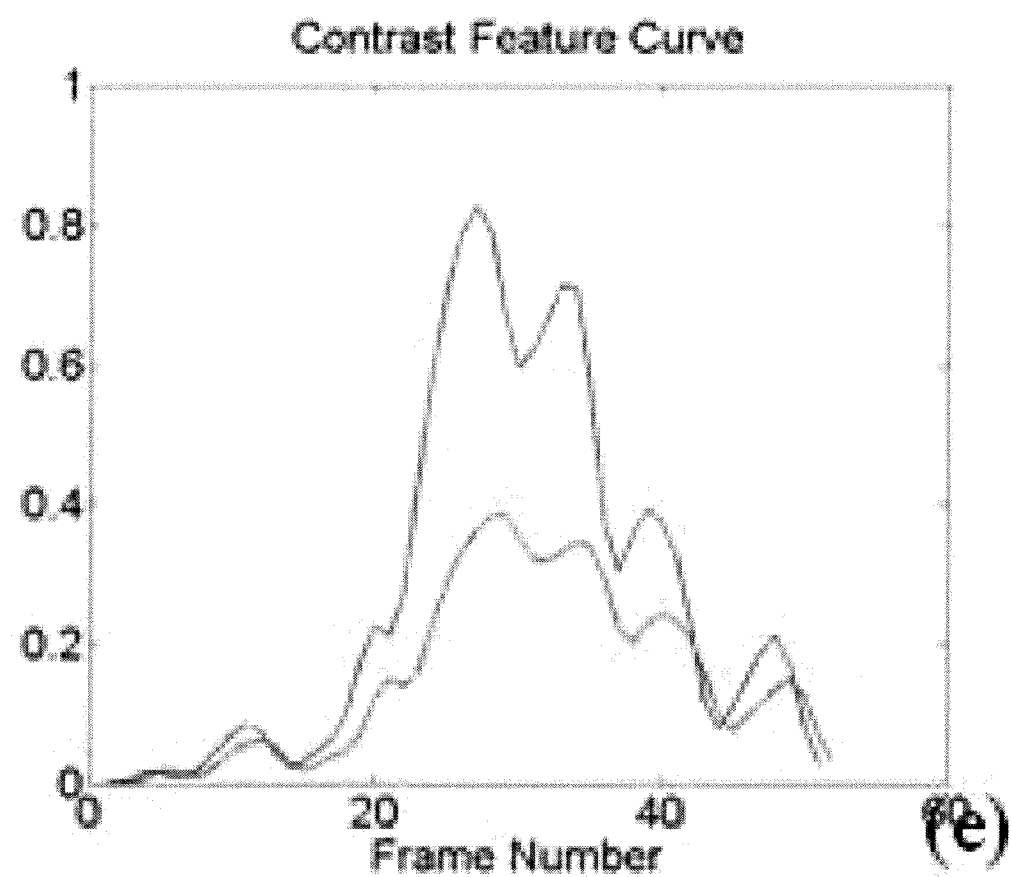

FIG. 5(e) is a graph illustrating an influence of an ultrasound probe on contrast feature curve calculation. The top curve is the feature curve without the TEE probe mask while the bottom curve is the feature curve with the TEE probe mask included.

Depending on the quality of the contrast injection, such influence on the absolute value of the contrast feature curve may not be a problem in some cases, but it can introduce a false negative for some sequences if the peak value is close to the threshold of contrast detection. In order to handle this problem, TEE probe may be detected and excluded from the calculation of the contrast feature value using Equation 1 below, where value 0 indicates the pixel as a in a probe mask. Because it is directly related to the calculation of the contrast feature curve, the criteria for a pixel to be classified as within the probe mask may be very strict. Specifically, for each pixel p in the ROI region there are three criteria: 1) its min intensity throughout the whole sequence, 2) the standard deviation of the intensity variation and 3) the absolute value of maximum intensity difference. Only if all the three values are within a proper range respectively will the pixel p will be counted as a probe mask pixel. The dark part in FIG. 5(d) indicates the detected TEE probe, which is not included in histogram computation. Although the mask covers a region smaller than 10% as shown in FIG. 5(d).

$$probeMask(p) = \begin{cases} 0 & \min(p) < t_{min} \ \& \ std(p) < t_{std} \ \& \ diff(p) < t_{diff} \\ 1 & \text{otherwise} \end{cases} \quad \text{(Eq. 1)}$$

After the probe has been detected and the probe mask generated in Step S102, the preliminary contrast-free X-ray image may then be used to produce an estimated background image (Step S103). The estimated background image may exclude the probe mask or alternatively, the probe mask may be used to identify the TEE probe within the background image.

The radiocontrast agent may then be administered (Step S104). Administration may be performed either prior to the start of the acquisition of the main sequence (Step S105), or shortly thereafter. The radiocontrast agent, which may be referred to herein simply as contrast, may be a substance that is easily detectable from within an X-ray image such as those acquired by the fluoroscope. While any suitable contrast may be used, an iodinated agent is an example of a suitable contrast. The contrast may be administered intravenously.

A main sequence of image frames may then be acquired (Step S105). This sequence may either include fluoroscopy or angiography images with N image frames. A determination may be made as to whether there is contrast injection in the aortic root in one or more frames of the sequence. The preliminary image frame(s) and the main sequence of image frames may, for example, be acquired from a single set of fluoroscopic images. However, to minimize the radiation does that the patient is exposed to; image acquisition may be stopped after the preliminary image has been acquired and before the main sequence of image frames is acquired. Additional sequences of image frames may be subsequently acquired and each sequence may be treated in a manner similar to or the same as the process described herein with reference to the main sequence of images. However, for the purposes of keeping the description simple, the process will be described herein with respect to a single main sequence of images even though it is to be understood that there may be additional sequences.

Global image brightness change may occur due to dose regulation in X-ray imaging systems, and mostly affects the first several frames of a sequence with contrast injection. However, at some occasions the problem can happen in the middle or throughout the whole sequence. If the sequence is non-contrasted, it may lead to a false positive, and if the sequence is contrasted, it may lead to a wrongly detected contrasted frame. With proper histogram mapping, the effect of brightness change in both situations can be handled. On the other hand, if histogram mapping is not done properly, the contrast injection may become faint and hence introduce false-negatives. Accordingly, exemplary embodiments of the present invention check the intensity variation and estimate the mapping from the region outside the ROI containing the aorta, and then apply the estimated map to the histogram within the ROI (Step S106).

Figure 2A:
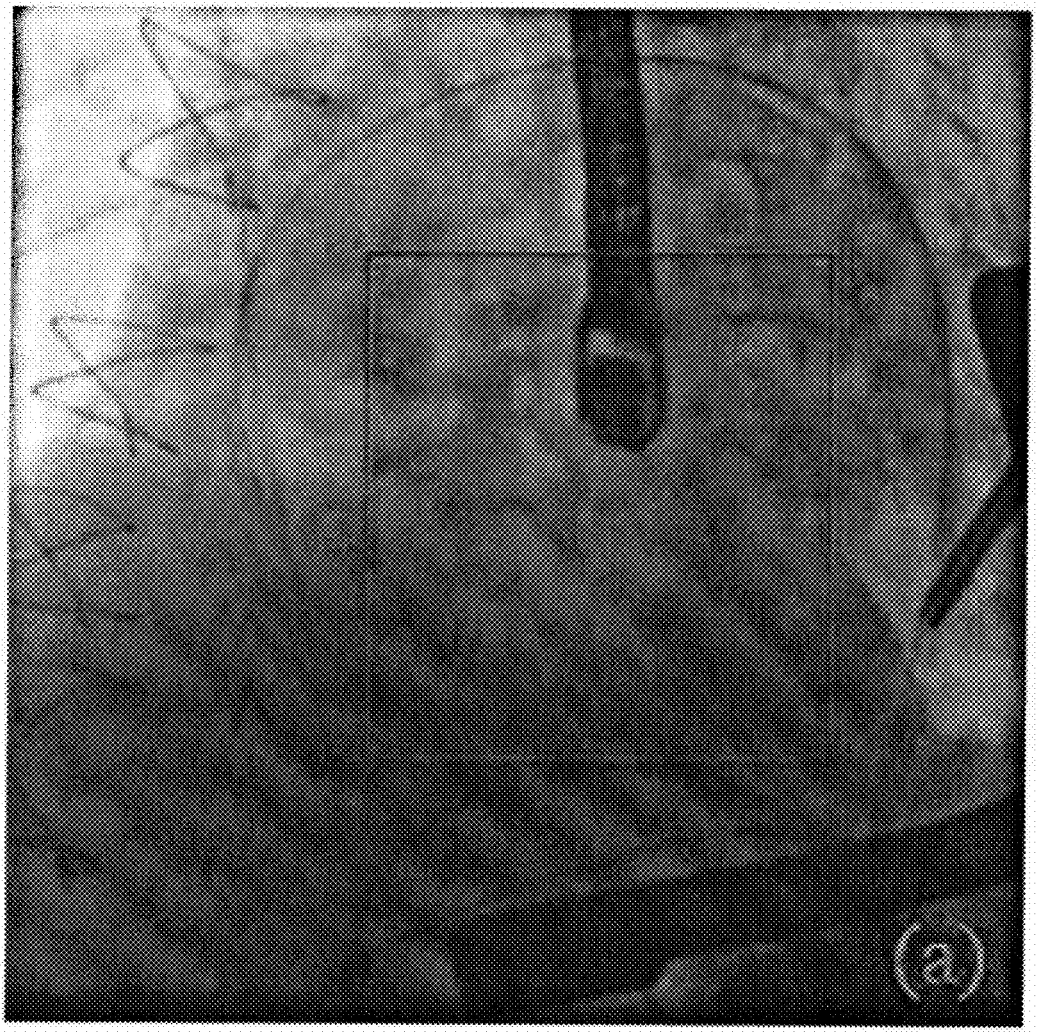
FIGS. 2(a)-(d) illustrate brightness check and mapping, on a non-contrasted sequence in accordance with exemplary embodiments of the present invention.
Figure 2B:
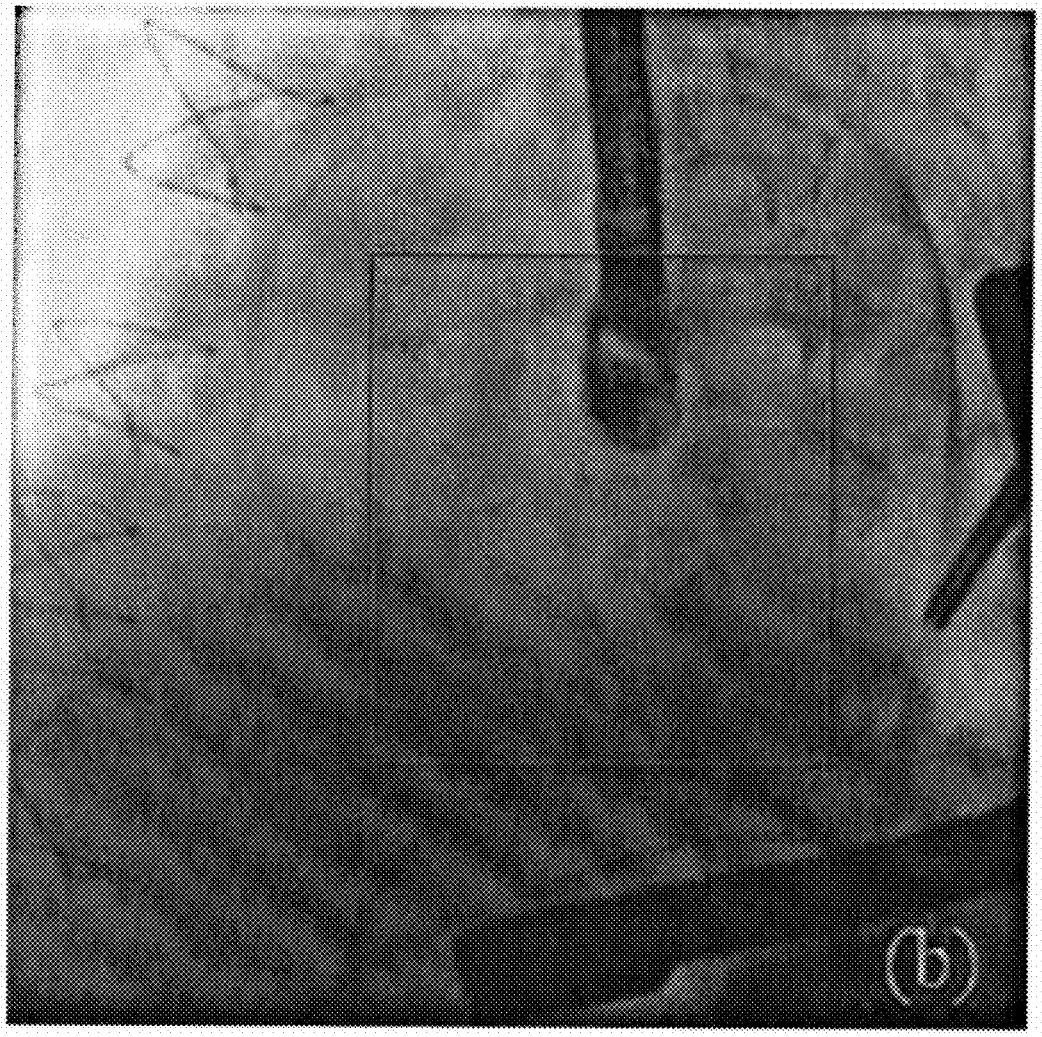
Figure 2C:
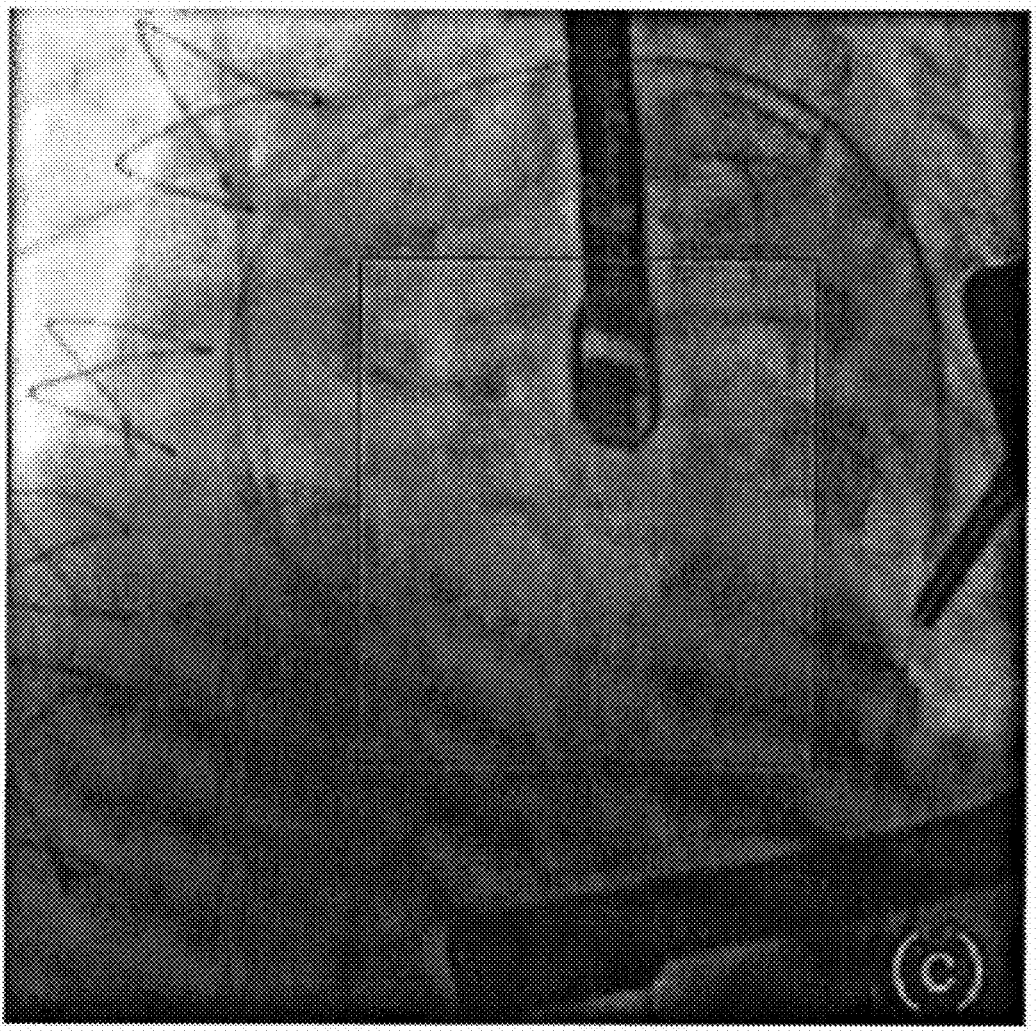
Figure 2D:
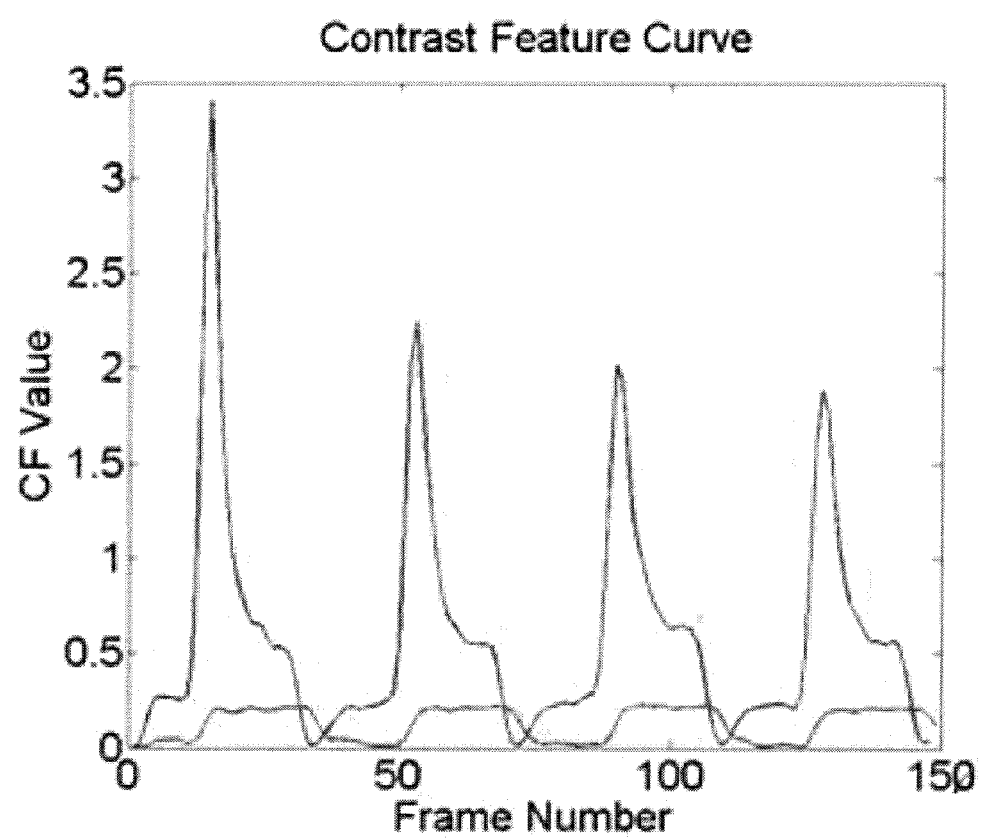

As shown in FIGS. 2(a)-(c) on which the box shape indicates the ROI region, if the mean intensity of each frame outside the ROI region varies noticeably across the sequence (e.g. larger than 7), histogram mapping may be applied within the ROI region. FIGS. 2 (a)-(c) illustrate a non-contrasted sequence within with a very large global brightness change is detected, and FIG. 2(d) shows a difference between the contrast feature curve with and without histogram mapping. From the curve, the pattern of periodic variation is clear, which is due to the patient's body tissue movement introduced by respiration. In FIG. 2(d) the top curve denotes the contrast feature curve without histogram mapping, showing a peak value over 3 and resulting a false positive. The bottom curve indicates the contrast feature curve with histogram mapping, showing a peak lower than 0.2 to avoid the false positive error.

FIGS. 2(a)-(d) illustrate brightness check and mapping, on a non-contrasted sequence. FIG. 2(a) depicts an original frame. FIG. 2(b) depicts the reference frame for histogram mapping. FIG. 2(c) depicts the same frame as in FIG. 2(a) but after histogram mapping. FIG. 2(d) depicts the contrast feature curve, on which the top curve indicates the result without histogram mapping, and the bottom curve indicates the result with histogram mapping.

The global brightness check of Step S106 may be used to adjust the brightness on the images of the main sequence when needed.

The resulting image frames may be examined to automatically detect the presence of contrast or, when necessary, to reject the entire sequence as not containing contrast. This analysis may either be performed while the set of images is acquired or immediately thereafter.

According to an exemplary embodiment of the present invention, monitoring of the image frames for the arrival of the contrast may be limited to a particular region within the sequence of main fluoroscopic images. This region should include the aortic root and the immediately surrounding area. This region may be referred to herein as either the region of interest (ROI) or the region of aorta (ROA). The ROA may be defined as a rectangular region that encloses the aortic root. Defining the ROA may be performed manually by a user or may be automatically derived, for example, from the C-arm CT volume position, when it is available.

The data set comprising the main set of fluoroscope images may either be obtained directly from the fluoroscope imager or it may be read from a disk. The data set may then be down-sampled for more efficient processing. For example, each frame may be reduced to 256×256 pixels. Thereafter the ROI of a size of approximately 128×128 pixels may be selected around the aortic root from the sequence. In this approach, the ROI selection need not be very precise. However, this information may be useful in facilitating the detection.

As discussed above with respect to Step S103, an estimated background image may be generated. The criteria of choosing the background image may be based on the intensity difference between the background (e.g. 75 percentile) and foreground intensity (e.g. 20 percentile). The estimated background image may be updated with background data from each image of the main sequence and may therefore be considered a mean background image.

The calculated mean background image may then be subtracted from each image frame of the set of X-ray images (Step S107) to produce a set of digitally subtracted images. For example, the j-th digitally subtracted image $SI_j$ may be calculated as:

$$SI_j = BI - I_j \quad \text{(Eq. 2)}$$

where $I_j$ is the j-th original frame, and BI is the calculated mean background image. Background and contrast image groups may then generated using a similar strategy as mentioned above, and background and contrast templates may be computed from the mean of the two groups, respectively. Based on the observation that the two templates contain rich information regarding the image sequence, several check steps highly related to the two templates may be utilized to increase the efficiency and accuracy.

Next, a measure of image intensity may be determined for each of the digitally subtracted images (Step S108). The image intensity may be determined, for example, by summing up the pixel intensity values of each pixel within the ROA. Alternatively, a histogram may be generated for each digitally subtracted image, where the histogram represents the distribution of pixel intensities within the subtracted image and the generated histograms may be used to determine the measure of image intensity for each subtracted image.

Next, it may be determined if the selected images exceed a predetermined measure of similarity with respect to the mean background image (Step S109). Close similarity between each of the selected images and the mean background image may be indicative of the absence of contrast within the main image set, and accordingly, such a determination may be used to end the analysis of the main image set. Exemplary embodiments of the present invention may utilize contrast and background templates which contain rich information about the sequence to determine the degree of similarity between selected images and the mean background image. If this information can be utilized properly to determine whether a sequence is with contrast or not, it can rule out a large group of non-contrast sequences, thus increasing processing efficiency.

This analysis of similarity between selected image and background may include a correlation test between the contrast and background template. For example, Equation 3 provided below may be used to perform the correlation test. Here $x_i$ denotes the histogram value for the background template and $y_i$ is the histogram value for the contrast template. A high correlation between these two values may indicate non-contrast (No, Step S109) and such a determination may end the search for contrast within the image set. Additionally, maximum indexes in the contrast and background templates may be compared to determine if the contrast and background are too similar, indicating non-contrast. In performing this comparison, close positioning of these two maximum indexes may be taken as an indication of non-contrast.

$$r_{xy} = \frac{n\sum_{i=1}^{n} x_i y_i - \sum_{i=1}^{n} x_i \sum_{i=1}^{n} y_i}{\sqrt{n\sum_{i=1}^{n} x_i^2 - \left(\sum_{i=1}^{n} x_i\right)^2} \sqrt{n\sum_{i=1}^{n} y_i^2 - \left(\sum_{i=1}^{n} y_i\right)^2}} \quad \text{(Eq. 3)}$$

As discussed above, in Step S108, an image intensity is determined for each subtracted image. An image of maximum image intensity may accordingly be selected. Next a predetermined shape model of the aorta may be fitted to the selected subtracted (Step S110). However, as an alternative to fitting the shape model (SM) to the image of maximum intensity, the SM may be matched to an average image of a set of multiple images including, for example, the image of maximum intensity, the frame immediately prior to the maximum intensity image and the frame immediately after the maximum intensity image. Alternatively, the SM may be matched to an average image of a set of the top three images of maximum intensity.

This averaging may be used to make the process algorithm more reliable by treating the three images in the contrast group as continuous. The images in the background group, however, may be spread out across all frames.

The pre-defined aorta shape model, SM, may be matched to the previously calculated contrast template by image-based 2-D/2-D registration.

In the 2-D/2-D registration of the SM to the contrast template, five parameters may be taken into consideration: scale in x- and y-direction, translation in x- and y-direction, and rotation. The optimal combination may be estimated by maximizing the difference between the average intensities within and outside the boundary of the aorta shape model as:

$$\hat{t} = \max_t \left( \frac{1}{N_{in}} \sum_{p \in SM} I_a(p) - \frac{1}{N_{out}} \sum_{p \notin SM} I_a(p) \right) \quad \text{(Eq. 4)}$$

A local optimization strategy such as hill climbing may be used to perform the fitting. However, exemplary embodiments of the present invention may alternatively, or additionally, use a semi-global optimization strategy for performing the shape fitting. First, with three different groups of scale and rotation parameters, a global search may be performed in the 2-D space of translation with a coarse grid. Next, starting from the optimal location obtained in the course grid search, a global search with all five parameters may be conducted in the region with the same size as one grid of the course grid. Then, a fine tuning may be performed using local optimization strategy of hill climbing algorithm in an even smaller region to get the best registration.

Figure 6A:
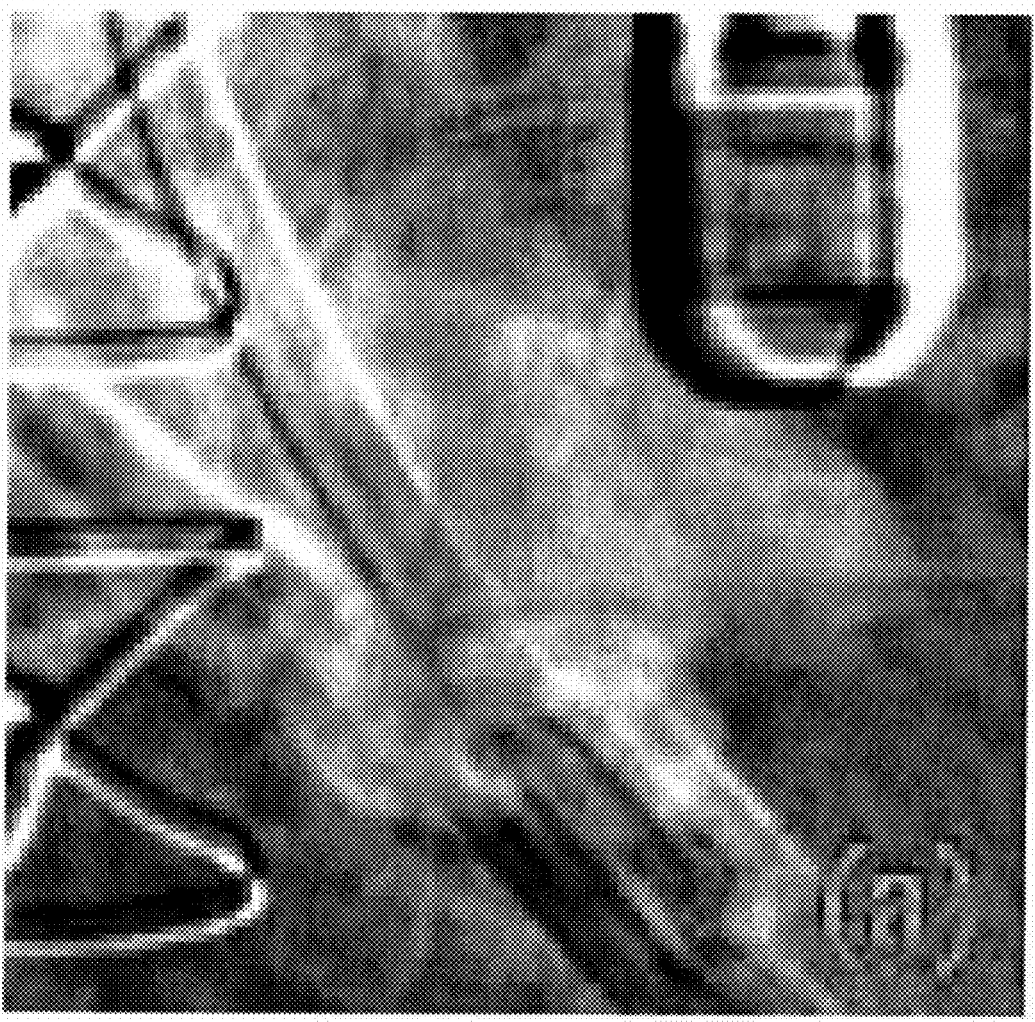
FIGS. 6(a)-(c) illustrate an example of the registration results on a faint contrasted frame in accordance with exemplary embodiments of the present invention.
Figure 6B:
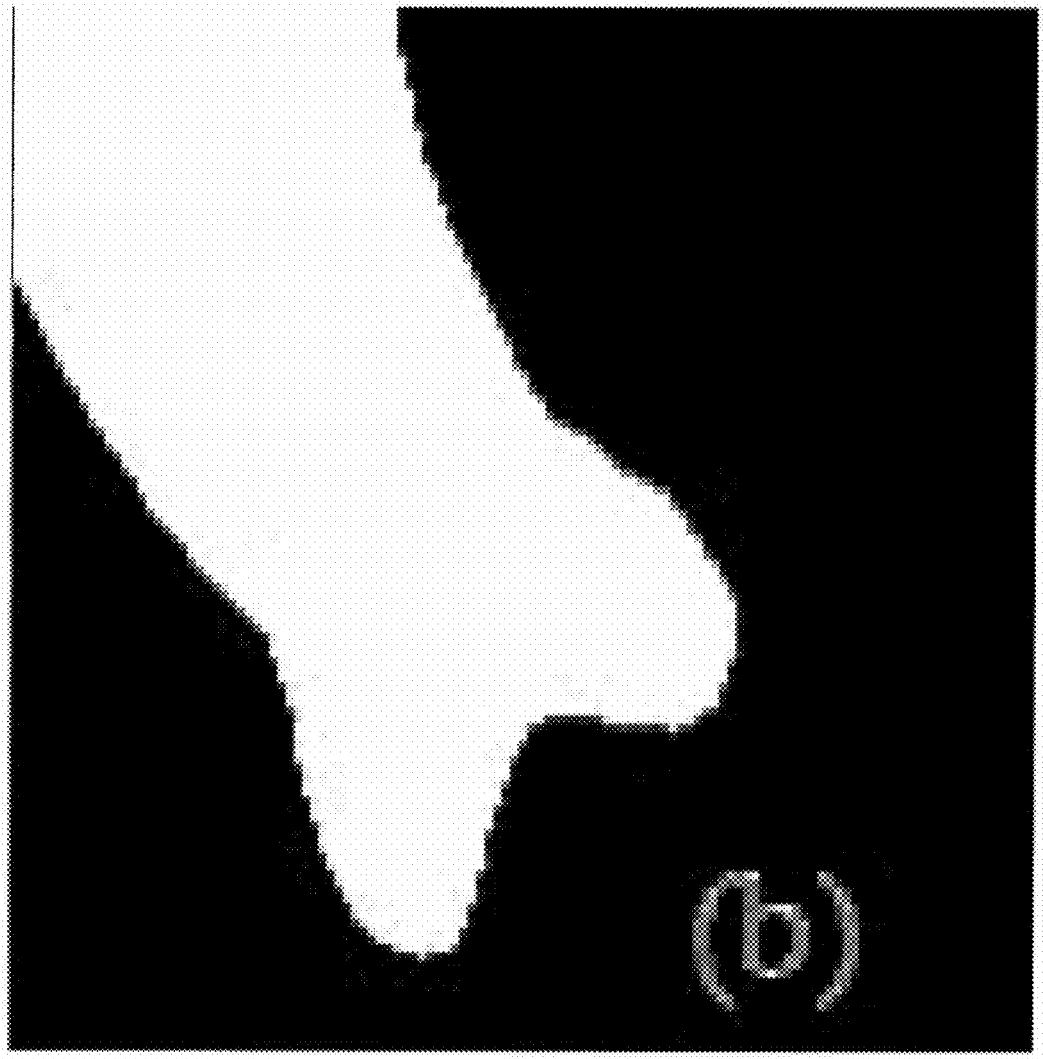
Figure 6C:
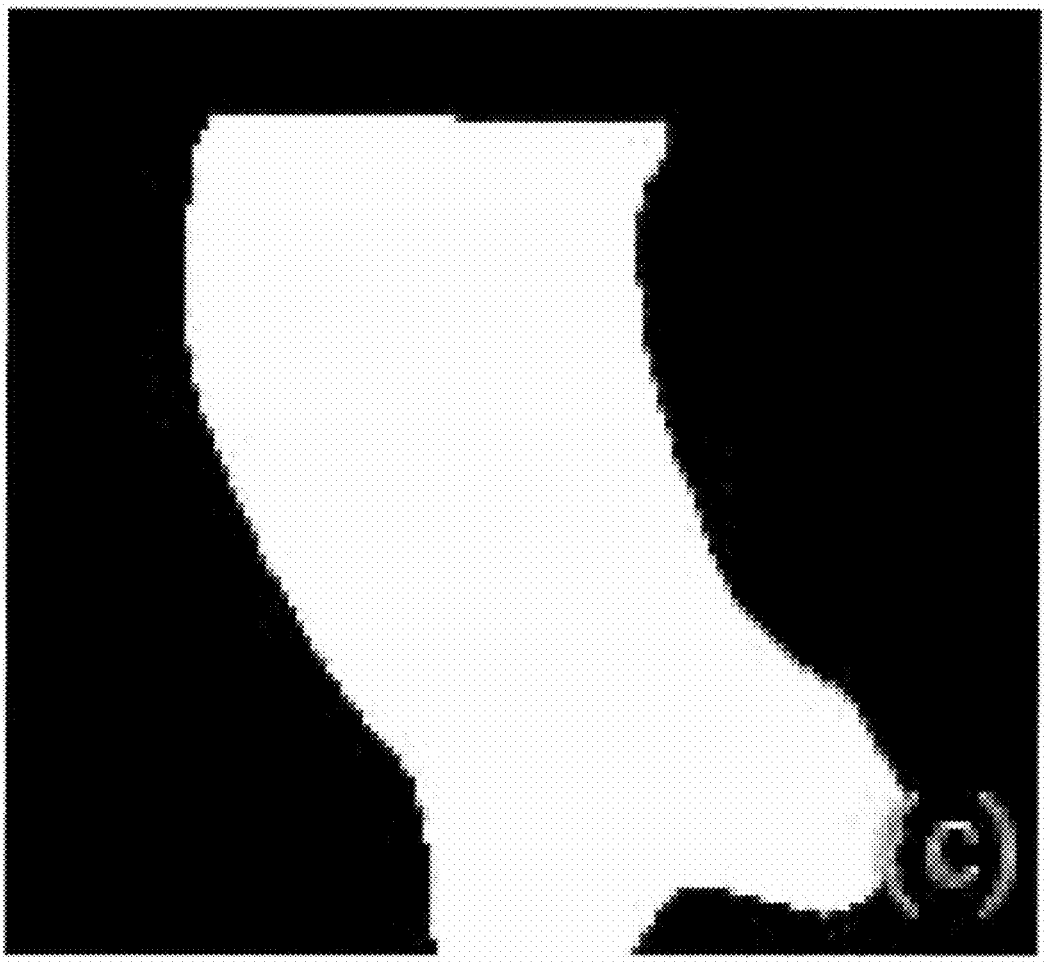

FIG. 6 illustrates an example of the registration results on a faint contrasted frame in accordance with exemplary embodiments of the present invention. The optimization strategy discussed herein may correctly register the SM. FIG. 6(a) illustrates the mean contrast template, FIG. 6(b) illustrates registration using the semi-global approach discussed herein, and FIG. 6(c) illustrates registration using a local optimization approach.

Once the SM has been fitted to the selected image (Step S110), this fitting may be used to fit the shape model to each subtracted image of the set (Step S111). Thereafter, analysis of the images for the presence of the contrast may be limited to the image pixels of the subtracted image corresponding to the placement of the fitted SM (the SM mask).

A check may then be performed to determine if there is correlation between the regions covered by the SM mask on the contrast and background templates (Step S112). In such a correlation test, a high correlation between them indicates non-contrast and/or a maximum value of the feature curve that is smaller than the predefined threshold may be taken to indicate non-contrast. In either event, if it is determined that there is a high correlation and thus non-contrast (Yes, S112) then the processing of the main sequence may be terminated without further analysis on the assumption that the set does not include contrast. If, however, no high correlation can be found (No, S112), the process may continue.

After no high correlation is found (No, S112), a feature curve may then be calculated (Step S113). The feature curve may be a temporal curve of the contrast feature where a contrast feature value $cf_j$ is calculated for frame j as an indication of the likelihood of its being a contrasted frame. The feature curve may be calculated based on the histogram similarity ratio as:

$$cf_j = S(HA_j, HA_{pc})/S(HA_j, HA_{nc}) \quad \text{(Eq. 5)}$$

where $S(HA_j, HA_{pc})$ is the similarity measure between the histogram of the current frame and the contrast template image, and $S(HA_j, HA_{pc})$ is the similarity measure between the histogram of the current frame and the background template image.

According to an exemplary embodiment of the present invention, the above contrast feature value may be multiplied with another piece of information named $cf_{offset}$: the histogram offset of the current frame to that of the background template. This information may be utilized based on the observation of the difference between the histograms of the contrasted frames and the background template. Compared to the histogram of the background template, the histogram of a contrasted frame has a larger shift into the high intensity region, while the histogram of a non-contrasted frame does not. The computation of $cf_{offset}$ for frame j is:

$$cf_{offset,j} = \sum_{i>max_b} H_j(i) - H_{background}(i) \quad (Eq. 6)$$

where $H_j(i)$ is the histogram bin at intensity i for frame j and $H_{background}(i)$ is the histogram bin at intensity i of the background template, and $max_b$ denotes the peak intensity of the background template.

To minimize the influence of the dark TEE probe on the calculation of $cf_j$, dark objects may be detected and excluded from the formation of histogram $SI_j$ with the help of probe mask detection of Step S102.

Thereafter, frequency analysis may be performed on the calculated feature curve cf (Step S114) to detect those false-positive cases caused by respiratory and cardiac motion. Frequency analysis may be performed, for example, by performing a Fast Fourier Transform (FFT) on the calculated feature curve. High contrast feature values representative of cardiac or respiratory motion may then be identified from the frequency analysis of the feature curve (Step S115).

Due to the nature of TAVI procedures, cardiac and respiratory motion effect may be inevitable in the X-ray images. Depending on the C-Arm angulations, the selection of ROI and whether or not the patient exhibits deep breathing, this motion may become significant and produce large peaks on the contrast feature curve, leading to false positives. Exemplary embodiments of the present invention may perform the frequency analysis on the contrast feature curve to detect the pseudo-cyclic signal at the frequency close to that of a typical cardiac and/or breathing motion.

In accordance with this approach, if one of these two peaks is found on the FFT of the contrast feature curve (Yes, Step S115), the sequence may be classified as non-contrasted and accordingly, the process of analyzing the present set may end. This criterion is based on the observation that the contrast medium injection in the X-ray sequences will greatly suppress the effect of respiration/heart and make it even unnoticeable on the contrast feature curve. In contrast when there is no contrast medium injection the effect of respiration and cardiac motion will be manifested. In particular, there are two parts in the criterion for detecting a peak on the FFT curve: a) the absolute value and b) the relative value to its neighbors. Both of them may exceed corresponding predetermined thresholds. The computation of the two values is shown below in Equation 6, where $\Omega$ indicates the neighbor of frequency k.

$$\hat{k} = \underset{k}{\operatorname{argmax}} \min(\||F(k)|-|F(k-1)\||, \||F(k)|-|F(k+1)\||) \quad (Eq. 7)$$

where $k = \{k \in K: k = \operatorname{argmax}_{k \in \Omega} |F(k)|\}$

For cases that the effect of respiration is not shown clearly on its FFT curve, such as where the absolute value is large enough while the relative value is not, a double check may be performed on the contrast feature curve using the local peak frequency detected from the FFT curve. For example, the contrast feature curve may be cut into several segments with the period according to the local peak frequency detected above. Cross correlation may be calculated among all the segments. If the correlation is above a certain threshold and the difference of their mean values is below a given value, then the sequence may be determined as a non-contrasted case with the local peak coming from cardiac and/or respiratory motion.

Figure 3A:
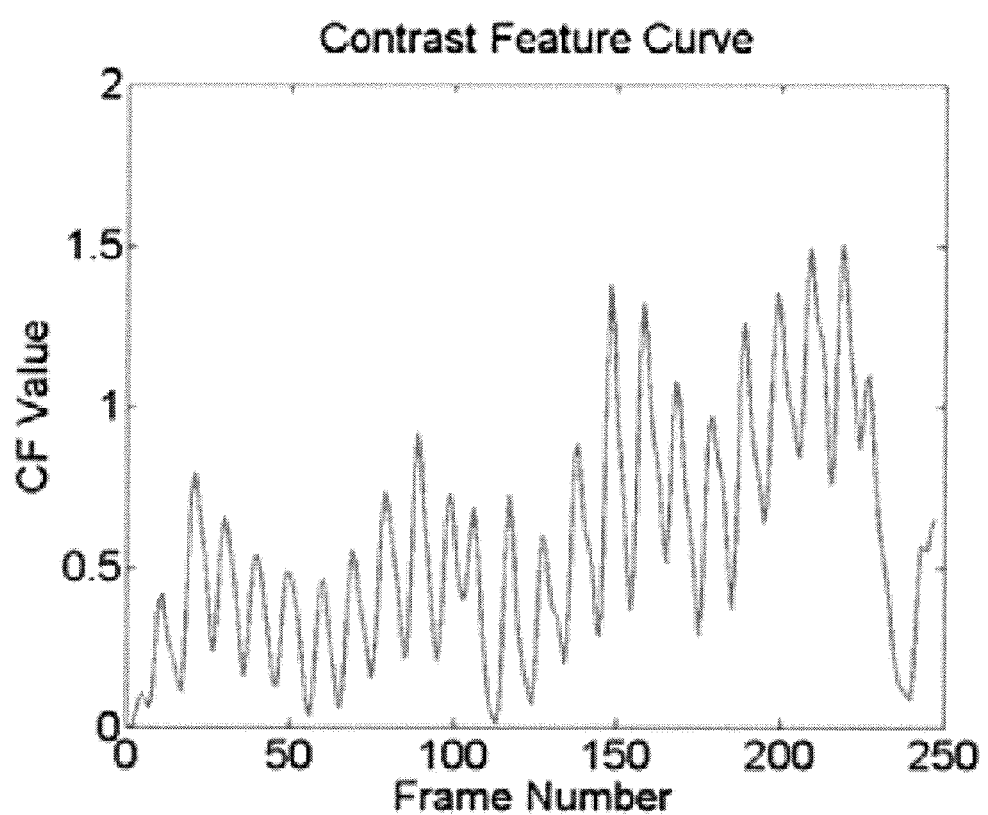
FIGS. 3(a)-(c) illustrate respiratory and cardiac motion, as identified in accordance with exemplary embodiments of the present invention.
Figure 3B:
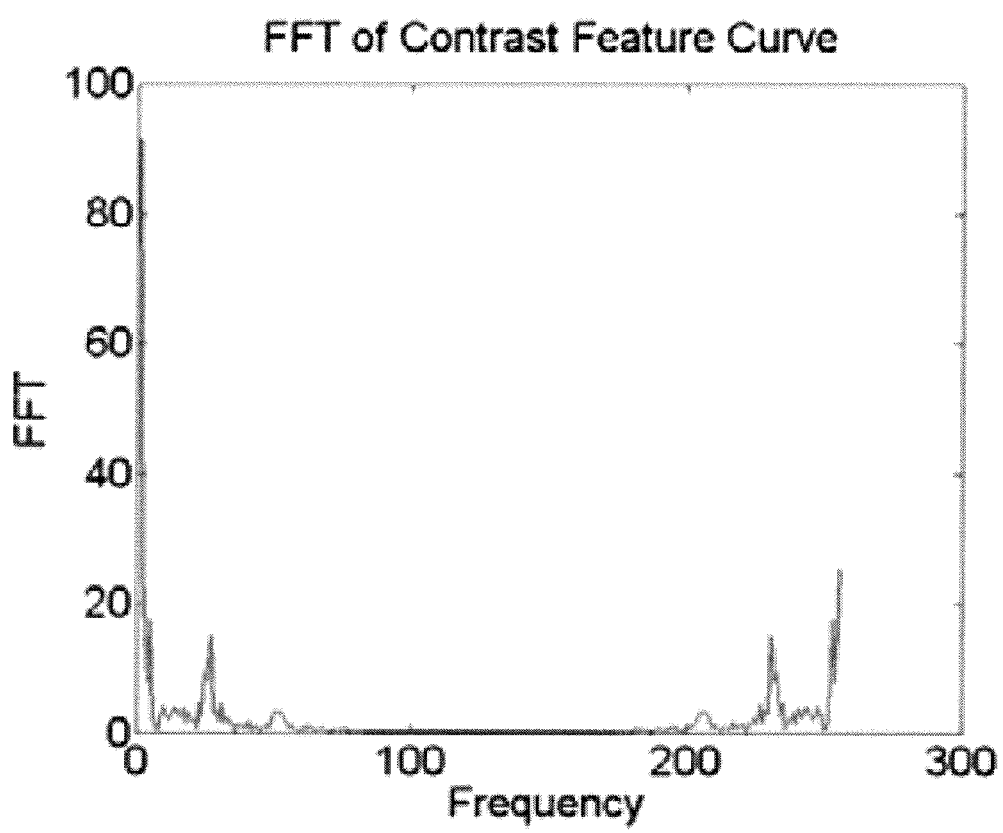
Figure 3C:
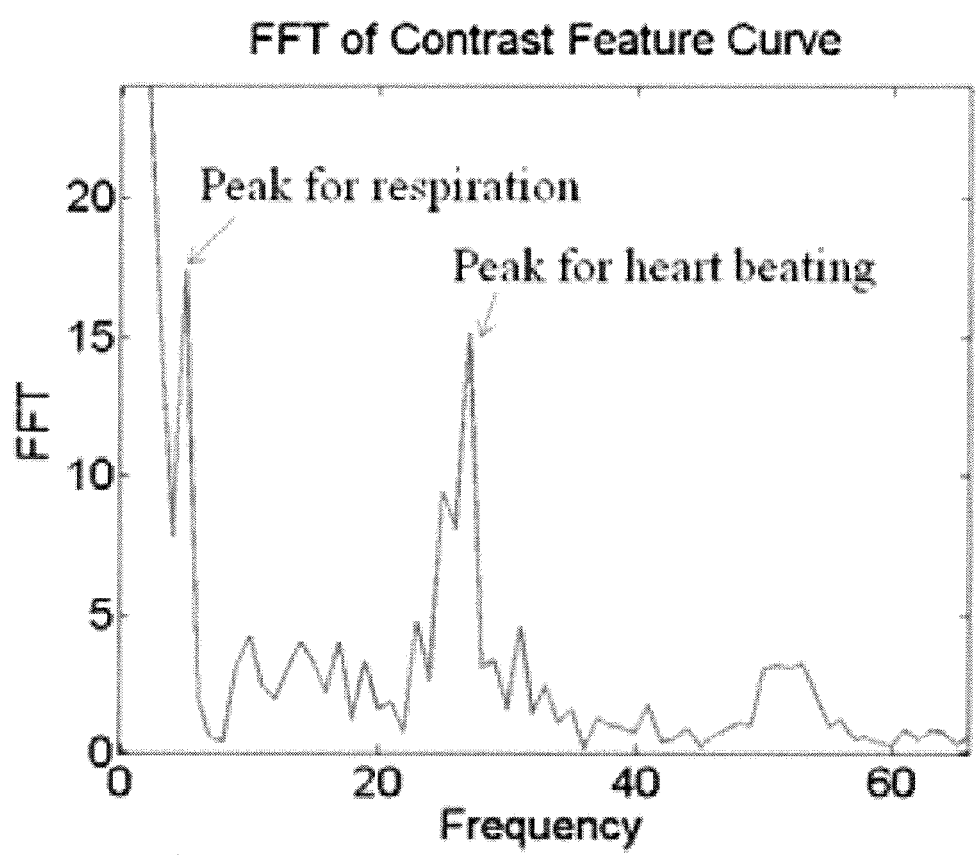

FIGS. 3(a)-(c) illustrate respiratory and cardiac motion, as identified in accordance with exemplary embodiments of the present invention. FIG. 3(a) illustrates the contrast feature curve of a non-contrasted sequence, FIG. 3(b) illustrates FFT of the contrast feature curve, and FIG. 3(c) illustrates a closer-look at the low frequency part of the FFT curve of FIG. 3(b).

Figure 4A:
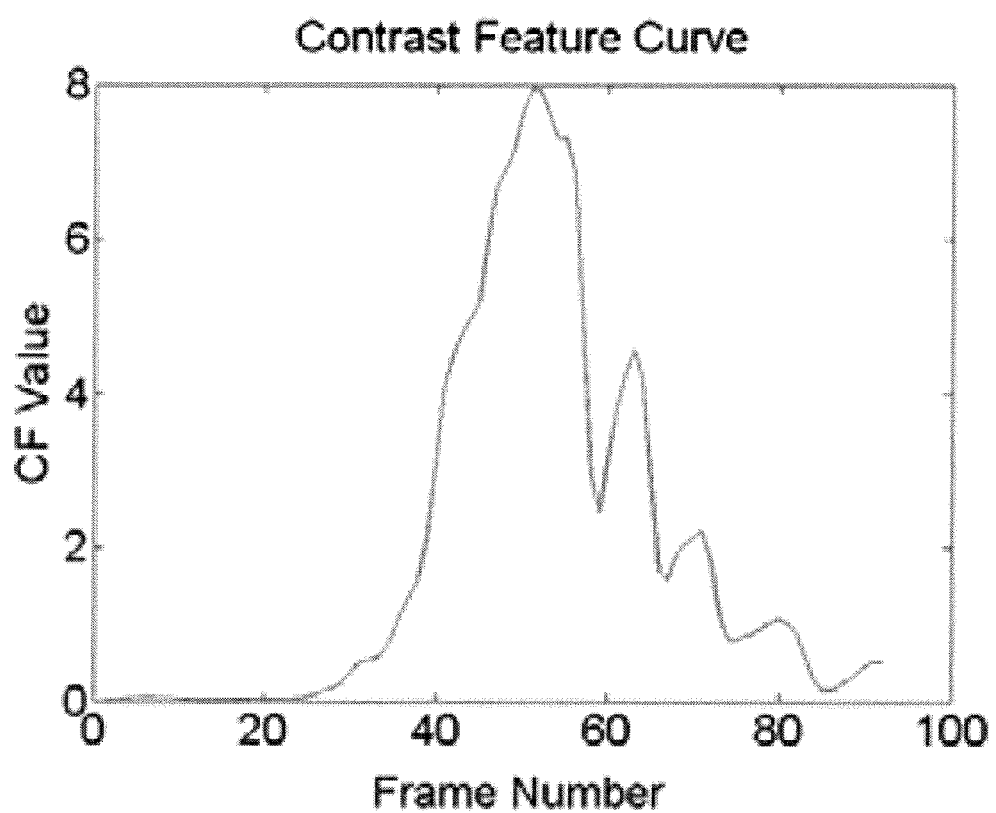
FIGS. 4(a)-(b) illustrate the contrast feature curve and its FFT for a contrasted sequence in accordance with exemplary embodiments of the present invention.
Figure 4B:
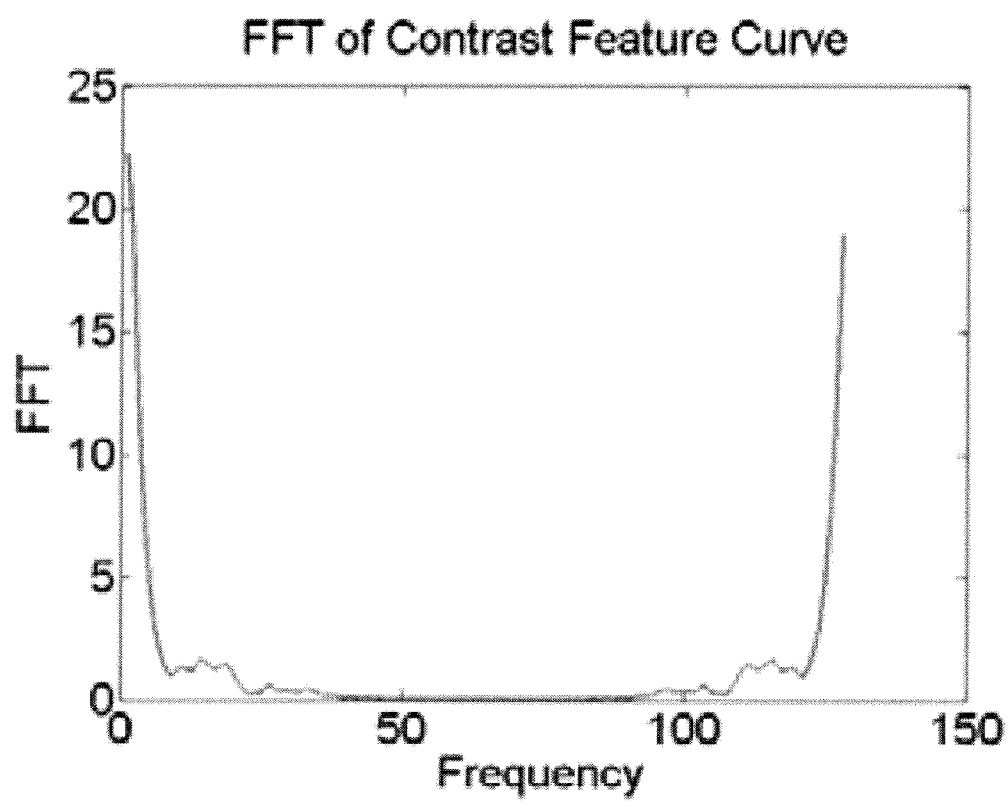

FIGS. 4(a)-(b) illustrate the contrast feature curve and its FFT for a contrasted sequence in accordance with exemplary embodiments of the present invention. FIG. 4(a) illustrates the contrast feature curve while FIG. 4(b) illustrates the FFT of the contrast feature curve.

In particular, FIG. 3(a) shows the feature curve of a typical non-contrasted sequence which is strongly affected by both the patient's respiration and heart beating. Unlike the feature curve in FIG. 2(d), where the effect of respiration dominates with a long cycle period and low frequency, the effect of heart beating is very clear in FIG. 3(a), which has a much shorter cycle period and hence higher frequency. In FIG. 3(b), the FFT of FIG. 3(a) is shown, and FIG. 3(c) is a close look at the low frequency part of FIG. 3(b). Two high local peaks can be found at the low frequency, representing respiration and heart beating respectively. The FFT of FIG. 2(d) has only one peak representing the respiration effect. FIG. 4 shows a contrasted sequence with a much smaller effect from respiration and heart beating, whose FFT curve does not show such high local peaks.

Where neither peal is found within the FFT of the contrast feature curve (No, Step S115), the sequence may be classified as contrasted and the frame(s) of peak contrast may then be identified from the image set (Step S116). The contrast feature curve may be used to identify the frame of peak contrast, for example, by identifying a peak within the curve.

After the main fluoroscopic image frames have been successfully monitored for the presence of contrast, this information may be used for the purpose of 2D-3D registration, for example, by selecting the frame of peak contrast for use in registration. It may also be beneficial, either for the purposes of performing image registration, motion compensation, or for other purposes, to identify the range of frames with sufficient contrast injection at the aortic root and ascending aorta.

Alternatively, a range of frames in which contrast fills the aortic root and ascending aorta that contain contrast may be identified given the detected peak of the contrast feature curve. Identification of non-contrasted frames may also be performed, and this data may together be used to train classifiers for identifying contrasted frames in sequent images.

The proposed method is not limited to AVI applications, and can be straightforwardly extended for other type of interventions and/or hybrid-OR applications As discussed above, exemplary embodiments of the present invention may serve multiple purposes. For example, the methods described above may be used to automatically detect whether there is contrast injection for one or more frames in a fluoroscopic and/or angiographic sequence. These methods may be used to automate the workflow to register 3D volumes onto fluoroscopic scenes. These methods may be used to automate the location of anatomical features only visible under contrast injections. These methods may be used to identify and use the most recent non-contrasted frame as the background to account for dynamic brightness level or scene changes in the sequence. These methods may be used to learn the contrasted template frame and non-contrasted template frame on-line from the current sequence. These methods may be used to generate a feature curve representing the likelihood of having contrast injection, which is invariant to various imaging physics and formation. These methods may be used to utilize a generic aorta shape that is easy to obtain off-line. The shape constraint may allow for separated histograms for contrasted and non-contrasted frames. These methods may be used to not only detect one contrasted frame in one sequence, but also to detect a range of usable frames for 2D/3D registration and motion compensation. These methods may be used to utilize the image-based information in the current sequence, and may require minimum prior models or learning. These methods may fast, cost-effective, and may involve minimum user interaction.

Figure 7:
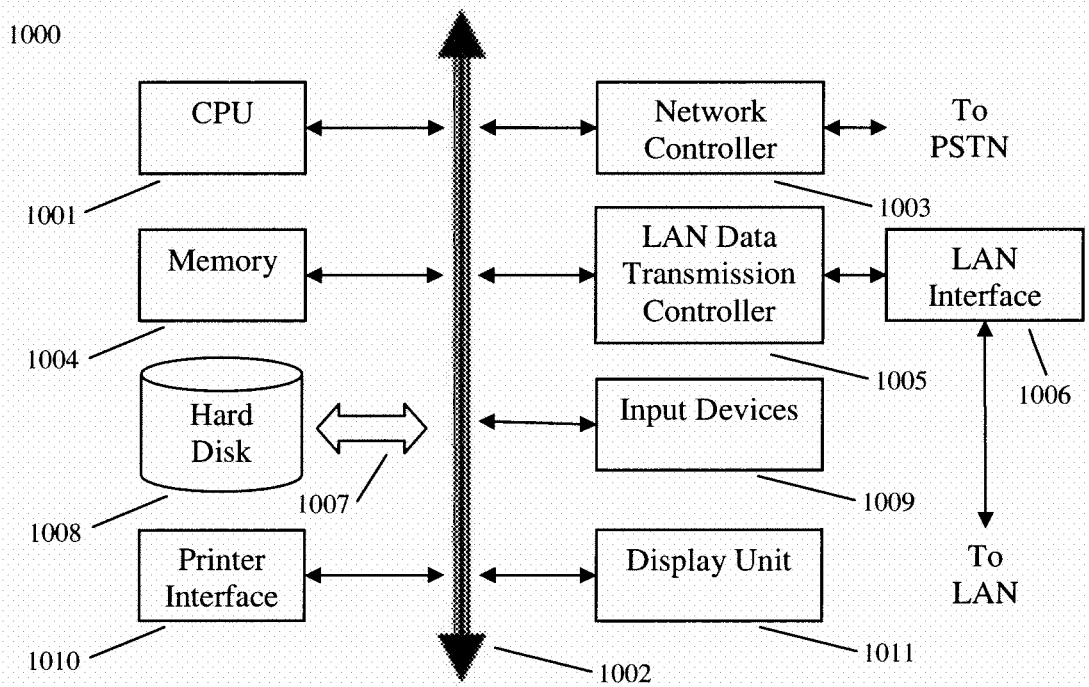
FIG. 7 shows an example of a computer system capable of implementing the method and apparatus according to embodiments of the present disclosure.

FIG. 7 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for automatically detecting the presence of a contrast agent in an x-ray image, comprising:

acquiring a preliminary x-ray image of a region of interest of a subject prior to administration of the contrast agent;

estimating a background image based on the acquired preliminary x-ray image;

administering the contrast agent into the subject;

acquiring a main set of x-ray images including a plurality of image frames;

subtracting the estimated background image from each image frame of the acquired main set of x-ray images to create a plurality of subtracted images corresponding to the plurality of image frames;

determining a measure of image intensity for each of the subtracted images;

selecting one or more of the subtracted images having a highest image intensity;

fitting a predefined shape model to the selected one or more subtracted images by using a semi-global optimization strategy;

using the fitting of the predefined shape model to the one or more subtracted images to fit the shape model to each of the plurality of subtracted images;

calculating a feature value for each image frame based on pixel intensities of each pixel fitted to the shape model for the corresponding subtracted image;

determining an image frame of peak contrast by selecting the image frame with the greatest feature value; and using the determined image frame of peak contrast to indicate the presence of the contrast agent in the main set of x-ray images, wherein the semi-global optimization strategy comprises:

performing a global search on a 2-D space of translation with a course grid using three different groups of five scale and rotation parameters to find a course-grid optimization;

starting from the course-grid optimization, performing a global search with all five scale and rotation parameters within a region defined by a size of one grid of the course grid to enhance the course-grid optimization; and performing fine-tuning of the enhanced course-grid optimization using a hill climbing algorithm as a local optimization strategy within a region that is smaller than the size of one grid of the course grid, wherein the five scale and rotation parameters include x-direction scale, y-direction scale, x-direction translation, y-direction translation, and rotation.

2. The method of claim 1, additionally comprising detecting a probe from within the preliminary x-ray image and generating a probe mask therefrom, and in calculating the feature value for each image frame based on pixel intensities of each pixel fitted to the shape model for the corresponding subtracted image, pixels corresponding to the generated probe mask are excluded.

3. The method of claim 1, wherein the estimation of the background is updated as the main set of x-ray images are acquired based on one or more most recent image frames that are classified as not including contrast.

4. The method of claim 1, wherein the measure of image intensity for each subtracted image includes generating a non-linear histogram mapping of each subtracted image.

5. The method of claim 4, wherein selecting one or more of the subtracted images having a highest image intensity includes determining one or more highest histogram values.

6. The method of claim 1, wherein the predefined shape model is modified in accordance with an anatomical structure of the subject prior to fitting.

7. The method of claim 1, wherein the predefined shape model represents an aortic root.

8. The method of claim 1, additionally comprising:

selecting a set of contrast frames from among the plurality of image frames that have a feature value that is sufficiently close to the frame of peak contrast;

selecting a set of non-contrast frames from among the plurality of image frames that have a feature value that is sufficiently far to the frame of peak contrast;

training a local classifier using the selected set of contrast
frames as positive training data and using the selected
set of non-contrast frames as negative training data; and
determining whether each of the frames of the plurality of
image frames that are neither sufficiently close to the
frame of peak contrast nor sufficiently far to the frame
of peak contrast are contrast frames or non-contrast
frames using the trained local classifier.

9. The method of claim 1, additionally comprising registering a 3D image of an aortic root to the image frame determined to be of peak contrast and displaying the registered image.

10. The method of claim 9, wherein the displayed registered image is used as visual guidance in performing an interventional procedure.

11. A method for automatically detecting a contrast agent in an x-ray image, comprising:
acquiring a preliminary x-ray image of a region of interest of a subject known to exclude the contrast agent;
detecting a probe from within the preliminary x-ray image and generating a probe mask therefrom;
estimating a background image based on the acquired preliminary x-ray image;
acquiring a first set of x-ray images including a plurality of image frames;
subtracting the estimated background image from each image frame of the acquired first set of x-ray images to create a plurality of subtracted images corresponding to the plurality of image frames;
determining a measure of image intensity for each of the subtracted images;
selecting one or more of the subtracted images having a highest image intensity;
comparing each of the selected images with the estimated background image and determining that the first set of x-ray images does not include the contrast when each of the selected images are within a predetermined measure of similarity to the background image, and when at least one of the subtracted images exceeds the predetermined measure of similarity to the background image, the following additional steps are performed:
fitting a predefined shape model to the selected one or more subtracted images using a semi-global optimization strategy;
using the fitting of the predefined shape model to the one or more subtracted images to fit the shape model to each of the plurality of subtracted images;
calculating a feature curve for set of x-ray images based on pixel intensities of each pixel fitted to the shape model for the corresponding subtracted image while excluding pixels corresponding to the generated probe mask;
performing frequency analysis on the calculated feature curve to identify a case in which high contrast feature value is attributable to cardiac or respiratory motion; and
when it is identified that the first set of x-ray images does not have a high contrast feature value attributable to cardiac or respiratory motion, the following additional step is performed:
determining an image frame of peak contrast by selecting the image frame with the greatest feature value,
wherein the determined image frame of peak contrast is used to indicate the presence of the contrast agent in the main set of x-ray images, and
wherein the semi-global optimization strategy comprises:
performing a global search on a 2-D space of translation with a course grid using three different groups of five scale and rotation parameters to find a course-grid optimization;
starting from the course-grid optimization, performing a global search with all five scale and rotation parameters within a region defined by a size of one grid of the course grid to enhance the course-grid optimization; and
performing fine-tuning of the enhanced course-grid optimization using a hill climbing algorithm as a local optimization strategy within a region that is smaller than the size of one grid of the course grid,
wherein the five scale and rotation parameters include x-direction scale, y-direction scale, x-direction translation, y-direction translation, and rotation.

12. The method of claim 11, wherein the estimation of the background is updated as the main set of x-ray images are acquired based on one or more most recent image frames that are classified as not including contrast.

13. The method of claim 11, wherein determining the measure of image intensity for each subtracted image includes generating a non-linear histogram mapping of each subtracted image.

14. The method of claim 13, wherein selecting one or more of the subtracted images having a highest image intensity includes determining one or more highest histogram values.

15. The method of claim 11, wherein the predefined shape model is modified in accordance with an anatomical structure of the subject prior to fitting.

16. The method of claim 11, wherein the predefined shape model represents an aortic root.

17. The method of claim 11, additionally comprising:
selecting a set of contrast frames from among the plurality of image frames that have a feature value that is sufficiently close to the frame of peak contrast;
selecting a set of non-contrast frames from among the plurality of image frames that have a feature value that is sufficiently far to the frame of peak contrast;
training a local classifier using the selected set of contrast frames as positive training data and using the selected set of non-contrast frames as negative training data; and
determining whether each of the frames of the plurality of image frames that are neither sufficiently close to the frame of peak contrast nor sufficiently far to the frame of peak contrast are contrast frames or non-contrast frames using the trained local classifier.

18. The method of claim 11, additionally comprising registering a 3D image of an aortic root to the image frame determined to be of peak contrast and displaying the registered image.

19. The method of claim 18, wherein the displayed registered image is used as visual guidance in performing an interventional procedure.

* * * * *